United States Patent
Liu et al.

(10) Patent No.: US 9,242,938 B2
(45) Date of Patent: Jan. 26, 2016

(54) GLYCINE REUPTAKE INHIBITOR AND USE THEREOF

(71) Applicant: Beijing Medisan Technology Co., Ltd., Changping District Beijing (CN)

(72) Inventors: Jinai Liu, Changping District Beijing (CN); Mingxin Wang, Changping District Beijing (CN); Fan Yang, Changping District Beijing (CN); Ailing Wang, Changping District Beijing (CN); Yan Zhu, Changping District Beijing (CN); Jin Cui, Changping District Beijing (CN); Lei Ji, Changping District Beijing (CN)

(73) Assignees: Beijing Medisan Technology Co., Ltd, Beijing (CN); Harbin Medisan Pharmaceutical Co., Ltd., Harbin (CN)

( * ) Notice: Subject to any disclaimer, the term of this patent is extended or adjusted under 35 U.S.C. 154(b) by 0 days.

(21) Appl. No.: 14/359,942

(22) PCT Filed: Nov. 21, 2012

(86) PCT No.: PCT/CN2012/084943
§ 371 (c)(1),
(2) Date: May 22, 2014

(87) PCT Pub. No.: WO2013/075624
PCT Pub. Date: May 30, 2013

(65) Prior Publication Data
US 2015/0133497 A1   May 14, 2015

(30) Foreign Application Priority Data

Nov. 22, 2011 (CN) .......................... 2011 1 0372769
Nov. 19, 2012 (CN) .......................... 2012 1 0469803

(51) Int. Cl.
*C07D 213/44* (2006.01)
*A61K 31/445* (2006.01)
*C07D 213/82* (2006.01)
*C07D 213/81* (2006.01)

(52) U.S. Cl.
CPC ............ *C07D 213/82* (2013.01); *C07D 213/81* (2013.01)

(58) Field of Classification Search
None
See application file for complete search history.

(56) References Cited

FOREIGN PATENT DOCUMENTS

| WO | 2005/037781 A2 | 4/2005 |
| WO | 2005/046601 A2 | 5/2005 |
| WO | 2011/023667 A1 | 3/2011 |

*Primary Examiner* — Heidi Reese
(74) *Attorney, Agent, or Firm* — Patrick J. Hagan; Dann, Dorfman, Herrell and Skillman

(57) ABSTRACT

Disclosed are a glycine reuptake inhibitor and the use thereof. The glycine reuptake inhibitor is a compound of formula I, or isomers, pharmaceutically acceptable salts or solvates thereof, wherein R1 is one or more groups selected from hydrogen, halogen, C1-6 alkyl, C1-6 alkoxy, nitro, cyano, amino, hydroxyl, C1-6 haloalkyl, and C1-6 haloalkoxy; R2 is selected from hydrogen, C1-6 alkyl, C1-6 alkoxy, C1-6 haloalkyl, and C1-6 haloalkoxy; and each of R3 and R4 is independently selected from hydrogen, halogen, C1-6 alkyl, C1-6 alkoxy, nitro, cyano, amino, hydroxyl, C1-6 haloalkyl, and C1-6 haloalkoxy.

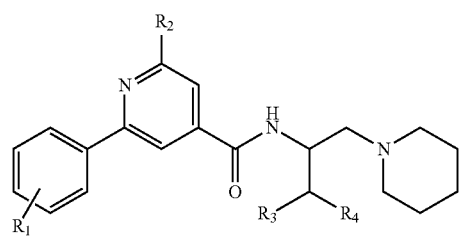

13 Claims, No Drawings

GLYCINE REUPTAKE INHIBITOR AND USE THEREOF

This application is a continuation-in-part of International Application No. PCT/CN2012/084943, which claims the benefits of priorities to Chinese patent application No. 201110372769.2 filed on Nov. 22, 2011 and Chinese patent application No. 201210469803.2 filed on Nov. 19, 2012.

TECHNICAL FIELD

The present invention relates to a glycine reuptake inhibitor and the use thereof, such inhibitors for example can be used to treat schizophrenic disorder.

BACKGROUND ART

Schizophrenic disorder is an extremely severe mental illness, lack of contact with reality, hallucinations, delusions and abnormal thinking, social functions significantly damaged. Schizophrenic disorder is a worldwide public hygiene issue; its total morbidity rate throughout the world (including China) is about 0.8-1%. The peak age of onset of schizophrenic disorder is 18~25 years old for men and 26~45 years old for women. However, patients having an onset during childhood, adolescence or even old age are also not rare. For different patients the severity and clinical manifestation of their symptoms differ from one another. Overall, the following three groups of symptoms can be summarized: positive symptoms, including hallucinations and delusions, agitation, paranoia, thinking disturbance and dystropy; negative symptoms, including affective blunting, uncommunicativeness, lack of interest, anhedonia andeccentric loner; cognitive deficits, including incapability to focus attention, severe decline of memory and incapability to behave as planned. One group or all the symptoms above may be present in a patient; these symptoms are usually relatively severe, which significantly affect work, interpersonal communication, and even personal life management of a patient. The general purpose of schizophrenic disorder treatment is to alleviate symptoms, prevent recurrence, restore functional defects, as much as possible to promote recovery and enhance life quality.

Currently drugs for treating schizophrenic disorder clinically may be mainly divided into two types: the first generation of anti-schizophrenic drugs (traditional antipsychotics). Such drugs mainly include selective dopamine D2 receptor antagonists, wherein the typical drugs are Haloperidol and Chlorpromazine and the like. These drugs have a certain therapeutic effect on the positive symptoms of schizophrenic disorder, but do not have any effect on the negative symptoms and cognitive deficits. Further, these drugs may lead to severe adverse reactions, such as extrapyramidal side effect, muscular rigidity and weight gain, etc. The second generation of anti-schizophrenic drugs (atypical antipsychotics). These drugs primarily are 5-hydroxytryptamine 5-HT2 receptor antagonists and dopamine D2 receptor antagonists, wherein the typical drugs for example are Olanzepine, Risperidone, Aripiprazole, Quetiapine and Clozapine. The second generation of atypical anti-schizophrenic drugs has a similar therapeutic effect on the positive symptoms of schizophrenic disorder to the first generation of anti-schizophrenic drugs, but has significantly less side effects such as extrapyramidal side effects.

At present anti-schizophrenic drugs used in clinic, particularly the second generation of atypical anti-schizophrenic drugs has a certain therapeutic effect on the positive symptoms of schizophrenic disorder, can alleviate or eliminate symptoms like hallucinations, delusions and thinking disturbance, etc. After the acute symptoms are eliminated, maintenance of antipsychotics can reduce the possibility of recurrence. However, almost all the clinical drugs have no significant therapeutic effect on the negative symptoms and cognitive deficits of schizophrenic disorder. Aripiprazole which is newly listed, as shown by the clinical study results, the drug may have a certain degree of therapeutic effect on the negative symptoms of schizophrenic disorder, but the therapeutic effect thereof is still non-significant and remains to be further investigated by clinical study. Additionally, anti-schizophrenic drugs can cause obvious adverse reactions, e.g. can lead to sedation, muscular rigidity, tremor and weight gain. Meanwhile these antipsychotics may cause tardive dyskinesia, a behavior which is characterized involuntarily by lip and tongue shrinkage, or twisting dyskinesia in arms and legs. Even after drug withdraw, the tardive dyskinesia would not disappear and lack of effective treatment measures.

Short-term prognosis (within one year) of schizophrenic disorder depends on the patient adherence to treatment. If without drug maintenance treatment, 70%~80% of schizophrenic disorder will relapse within 12 months and may attack again. Drug maintenance may reduce the recurrence rate of the present disease down to about 30%.

Long-term prognosis of schizophrenic disorder greatly varies, wherein ⅓ of patients may obtain significant and sustained improvement, and for another ⅓ of patients, conditions are partially improved with intermittent onsets and left with disabilities, and for the remaining ⅓ of patients, conditions are severe with obvious disabilities. Factors of good prognosis include patients with acute onset, late age of onset, good social skills before onset, and paranoid or positive schizophrenic disorder. Factors of poor prognostic include patients with early age of onset, poor social or professional skills before onset, positive family history of schizophrenic disorder as well as hebephrenic or negative schizophrenic disorder.

CN101616592A has disclosed a benzotriazinone compound for enhancing glutamatergic synaptic responses, which may be used to prevent and treat cerebral insufficiency, for example various diseases such as dementia, schizophrenic disorder and the like. CN101035760A has disclosed a compound for enhancing glutamate receptors, which can be used to treat schizophrenic disorder. CN1535980A has disclosed a novel compound having inhibitory activity against glycine transporter, useful to treat schizophrenic disorder.

Currently, new methods for treating schizophrenic disorder are still expected in the art.

SUMMARY OF THE INVENTION

The object of the present invention lies in providing a novel glycine reuptake inhibitor and expecting it can be used effectively in treating schizophrenic disorder. The present invention has surprisingly found that a compound shown in formula I has an effective glycine reuptake inhibitory activity, based on which the present invention is completed.

In the first aspect of the present invention, provided are the following compounds of formula I,

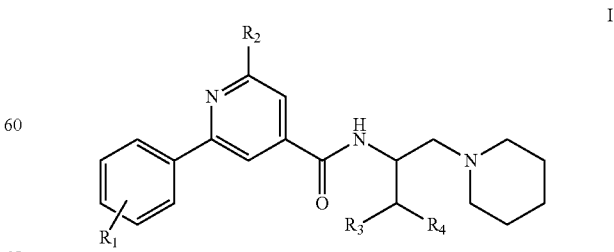

or isomers, pharmaceutically acceptable salts or solvates thereof, wherein

R1 is one or more groups each independently selected from: hydrogen, halogen, C1-6 alkyl, C1-6 alkoxy, nitro, cyano, amino, hydroxyl, C1-6 haloalkyl, and C1-6 haloalkoxy;

R2 is selected from: hydrogen, C1-6 alkyl, C1-6 alkoxy, C1-6 haloalkyl, and C1-6 haloalkoxy;

R3 and R4 are each independently selected from hydrogen, halogen, C1-6 alkyl, C1-6 alkoxy, nitro, cyano, amino, hydroxyl, C1-6 haloalkyl, and C1-6 haloalkoxy.

A compound according to the first aspect of the present invention, wherein R1 is selected from: halogen, hydroxyl, C1-6 alkyl, C1-6 alkoxy, C1-6 haloalkyl and C1-6 haloalkoxy.

A compound according to the first aspect of the present invention, wherein R2 is selected from: C1-6 alkyl and C1-6 alkoxy.

A compound according to the first aspect of the present invention, wherein R3 and R4 are each independently selected from: hydrogen, C1-6 alkyl, C1-6 alkoxy and hydroxyl.

A compound according to the first aspect of the present invention, wherein the C1-6 alkyl is a C1-4 alkyl.

A compound according to the first aspect of the present invention, wherein the halogen (halo) is selected from fluorine, chlorine, bromine, iodine, preferably fluorine and chlorine.

A compound according to the first aspect of the present invention, which is a compound selected from:

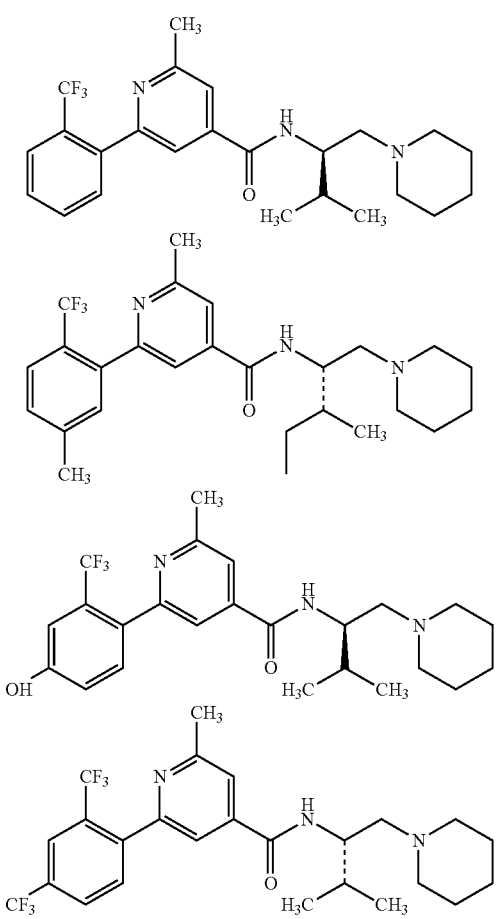

-continued

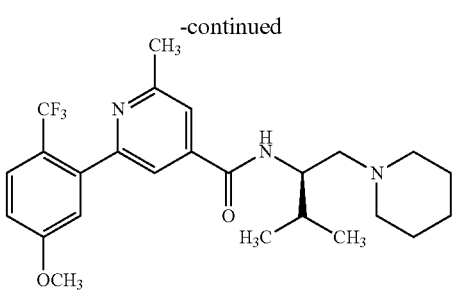

The second aspect of the present invention relates to a method for preparing the compound described in the first aspect of the present invention The third aspect of the present invention relates to a pharmaceutical composition, comprising the compound of formula I of any one of the first aspect of the present invention and optionally one or more pharmaceutically acceptable carriers or excipients.

The fourth aspect of the present invention relates to the use of the compound of formula I of any one of the first aspect of the present invention in preparing drugs of glycine reuptake inhibitor. The fourth aspect of the present invention also relates to the use of the compound of formula I of any one of the first aspect of the present invention in preparing drugs for treating and/or preventing schizophrenic disorder in a mammal (including human).

The fifth aspect of the present invention relates to a method for treating and/or preventing mammal (including human) schizophrenic disorder in a mammal in need thereof. The method comprises administering a therapeutically effective amount of the compound of formula I of any one of the first aspect of the present invention to a mammal in need thereof.

The sixth aspect of the present invention relates to a pharmaceutical composition for treating and/or preventing schizophrenic disorder in a mammal (including human). The pharmaceutical composition comprises the compound of formula I of any one of the first aspect of the present invention and optionally one or more pharmaceutically acceptable carriers or excipients.

The seventh aspect of the present invention also relates to the compound of formula I of any one of the first aspect of the present invention for treating and/or preventing schizophrenic disorder in a mammal (including human).

Any embodiment in any aspect of the present invention may be in combination with other embodiments, provided that they do not have a contradictory. Further, in any embodiment in any aspect of the present invention, any technical feature may be suitable for the technical feature in other embodiments, provided that they do not have a contradictory.

Hereinafter, the present invention will be further described.

All the documents cited by the present invention are hereby incorporated by reference in their entirety, and if a meaning expressed in these documents is inconsistent with the present invention, the statement of the present invention is taken as the standard. Further, various terms and phrases used in the present invention have the general meaning commonly known by those skilled in the art. Even so, the present invention still expects to illustrate and explain these terms and phrases more detailedly herein. If there are terms and phrases mentioned inconsistent with the meanings commonly known, the meanings stated in the present invention are taken as the standard.

In the method for synthesizing the compound of formula I of the present invention, various raw materials used in the reaction can be prepared by those skilled in the art according to the prior knowledge, or prepared via methods commonly known in the references, or purchased commercially. The intermediates, raw materials, reagents and reaction conditions, etc. used in the reaction scheme above may be properly changed according to the prior knowledge of those skilled in the art. Alternatively, those skilled in the art may also synthesize the other compounds of formula I unlisted specifically in the present invention according to the method in the second aspect of the present invention.

The compound of formula I of the present invention can be used in combination with other active ingredients, provided that it does not produce other adverse effects such as hypersensitive response.

The active compound shown in the formula I of the present invention may be used as an anti-schizophrenia drug alone, or used in combination with one or more other anti-schizophrenia drugs. Combination treatment is achieved by simultaneously, sequentially or separately administrating various therapeutic components.

The term "composition" as used herein is intended to include the product comprising a designated amount of each designated ingredient, and any product directly or indirectly produced from combinations of the specified amount of each specified ingredient. In the present invention, the term "composition" may be used interchangeably with "pharmaceutical composition".

The compounds of the present invention may be used in the form of pharmaceutically acceptable salts derived from inorganic acids or organic acids. The phrase "pharmaceutically acceptable salt" refers to a salt within the scope of sound medical judgment suitable for use in contacting with tissues of humans and lower animals without undue toxicity, irritation and hypersensitive response, etc. and is commensurate with a reasonable effect/risk ratio. Pharmaceutically acceptable salts are commonly known in the art. For example, pharmaceutically acceptable salts are described detailedly in S. M. Berge, et al., J. Pharmaceutical Sciences, 1977, 66: 1. The salts may be prepared in situ or separately by reacting the free base functionality of the compounds of the present invention with a suitable organic acid during the final isolation and purification processes of the compound of the present invention. Representative acid addition salts include but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodic, 2-hydroxylethanesulfonate (isothionate), lactate, maleate, methanesulfonate, nicotinate, 2-naphthalenesulfonate, oxalate, palmitate, pectate, persulfate, 3-phenylpropionate, picrate, pivalate, propionate, succinate, tartrate, thiocyanate, phosphate, glutamate, bicarbonate, p-toluenesulfonate and undecanoate. Likewise, the basic nitrogen-containing group may be quaternized with following substances: lower alkyl halides such as chlorides, bromides and iodides of methyl, ethyl, propyl and butyl; dialkyl sulfates such as dimethyl, diethyl, dibutyl and diamyl sulfates; long-chain halides such as chlorides, bromides and iodides of decyl, lauryl, myristyl and stearyl; arylalkyl halides such as benzyl bromide and phenethyl bromide and others. Thus products able to be dissolved or dispersed in water or oil are obtained. Examples of acid used to form pharmaceutically acceptable acid addition salts include inorganic acids such as hydrochloric acid, hydrobromic acid, sulfuric acid and phosphoric acid, and organic acids such as oxalic acid, maleic acid, succinic acid and citric acid.

Base addition salts may be prepared in situ during the final isolation and purification processes of the compound of the present invention, by reacting the carboxyl-containing moiety in the compound of the present invention with a suitable base. The base is exemplified as a hydroxide, carbonate or bicarbonate of a pharmaceutically acceptable metal cation, or ammonia or an organic primary amine, secondary amine or tertiary amine Pharmaceutically acceptable salts include but are not limited to the salts based on alkali metal or alkaline-earth metal cations such as lithium, sodium, potassium, calcium, magnesium and aluminum, etc., and non-toxic quaternary ammonium and amine cations including ammonium, tetramethyl ammonium, tetraethyl ammonium, methyl ammonium, dimethyl ammonium, trimethyl ammonium, triethyl ammonium, diethyl ammonium and ethyl ammonium and the like. Other representative organic amines for forming the base addition salts include ethylenediamine, ethanol amine, diethanol amine, piperidine and piperazine, etc.

The compounds of formula I of the present invention also include the isomers, racemates, enantiomers, diastereomer, enantiomer enrichments, solvates and esters thereof. The compounds of formula I of the present invention and the isomers, racemates, enantiomers, diastereomer, enantiomer enrichments, solvates and esters thereof may also form solvates, for example hydrates, alcoholates and the like. The aforementioned compounds also may be prodrugs or the forms able to release said active ingredients after metabolic changes in vivo. Selecting and preparing a suitable prodrug derivation is a commonly known technology for those skilled in the art. In general, for the purpose of the present invention, solvated forms with pharmaceutically acceptable solvents such as water, ethanol and the like are equivalent to unsolvated forms.

The actual dosage level of each active ingredient in the composition of the present invention may be changed so that the resulting amount of active compounds can effectively direct to a specific patient, composition and mode of administration obtain a desired therapeutic response. The dosage level must be selected according to the activity of the specific compound, administration route, the severity of conditions under treatment as well as conditions and anamnesis of patients to be treated. However, the practice in the art is that the compound dosage begins with a lower level than that required to obtain the desired therapeutic effect and then gradually increases until obtaining the desired effect.

When used for the aforementioned treatment and/or prevention or other treatments and/or preventions, the therapeutically and/or prophylactically effect amount of a compound of the present invention may be used in pure form or used in the form of pharmaceutically acceptable ester or prodrug (in the case that these forms exist). Alternatively, the compound may be administrated as a pharmaceutical composition containing the object compound with one or more pharmaceutically acceptable excipients. The term "a therapeutically and/or prophylactically effect amount" of the compound of the present invention refers to an enough amount of compound applicable to any medical therapeutically and/or prophylactically reasonable effect/risk ratio. But it should be understood that the total daily dose of the compound and composition of the present invention must be determined by attending physician within the scope of sound medical judgment. For any specific patient, the specific therapeutically effect dosage level must be determined according to various factors, which include the disorder to be treated and the severity of the disorder; the activity of the specific compound employed; the specific compound employed; age, weight, general health condition, gender and diet of the patient; the administration time, administration route and excretion rate of the specific compound employed; treatment duration; drugs used in combination with or simultaneously with the specific compounds employed; and the similar factors commonly known in the medical art. For example, the practice of the present art is that the compound dosage begins with a lower level than that required to obtain the desired therapeutic effect and then gradually increases until obtaining desired effect. In general, the dosage of the compound of formula I of the present invention for a mammal particularly human may be between 0.001~1000 mg/kg body weight/day, such as between 0.01~100 mg/kg body weight/day, or such as between 0.01~10 mg/kg body weight/day.

By applying pharmaceutical carriers well known by those skilled in the art, the pharmaceutical composition containing an effective amount of the compound of the present invention may be prepared. Therefore, the invention also provides a pharmaceutical composition containing the compound of the present invention formulated together with one or more non-toxic pharmaceutically acceptable carriers. The pharmaceutical composition may be particularly formulated into a solid or liquid form for oral administration, for parenteral injection, or for rectal administration.

The pharmaceutical composition may be formulated into many dosage forms for convenient administration, for example oral preparations (such as tablets, capsules, solutions or suspensions); injectable preparations (such as injectable solutions or suspensions, or injectable dry powder, able to be used immediately by adding water for injection prior to injection). The carriers used in the pharmaceutical composition include: binders used in oral preparations (such as starch, typically corn, wheat or rice starch, gelatin, methyl cellulose, sodium carboxymethyl cellulose and/or polyvinylpyrrolidone), diluents (such as lactose, dextrose, sucrose, mannitol, sorbitol, cellulose and/or glycerol), lubricants (such as silica, talc, stearic acid or a salt thereof, typically magnesium stearate or calcium stearate, and/or polyethylene glycol), and if needed, also contained are disintegrants such as starch, agar, alginic acid or a salt thereof, typically sodium alginate, and/or an effervescent mixtures, solubilizers, stabilizers, suspending agents, with/without coloring agents, corrigents, etc., preservatives, solubilizers and stabilizers, etc. used in injectable formulations; matrix, diluent, lubricants and preservatives, etc. used in topical formulations. Pharmaceutical formulations may be administered via oral or parenteral (e.g., intravenous, subcutaneous, intraperitoneal or topical) route. If some drugs are unstable under the conditions of stomach, it may be formulated into enteric-coated tablets.

More particularly, the pharmaceutical composition of the present invention may be administrated to a human or other mammal by oral, rectal, parenteral, enteral, intravaginal, intraperitoneal, topical (such as by powders, ointments or drops), buccal administrations, or administrated as a oral spray or nasal spray. As used herein, the term "parenteral" refers to the administration modes including intravenous, intramuscular, intraperitoneal, intrasternal, subcutaneous and intraarticular injection and infusion.

The composition suitable for parenteral injection may comprise physiologically acceptable sterile aqueous or non-aqueous solutions, dispersants, suspensions or emulsions, and sterile powders for use in reconstituting into sterile injectable solutions or dispersants. The examples for suitable aqueous or non-aqueous carriers, diluents, solvents or vehicles include water, ethanol, polyols (propylene glycol, polyethylene glycol and glycerol, etc.), vegetable oils (such as olive oil), injectable organic esters such as ethyl oleate and suitable mixtures thereof.

These compositions may also contain adjuvant agents such as preservatives, wetting agents, emulsifiers and dispersants. By means of various anti-bacterial and antifungal agents, for example, parabens, trichlorotert-butanol, phenol and sorbic acid, etc., the effect of preventing microorganisms can be ensured. It is also expected to include an isotonic agent, for example sugars, sodium chloride, etc. By use of a substance able to delay absorption, for example aluminum monostearate and gelatin, extended absorption of the injectable pharmaceutical form can be achieved.

Suspensions, in addition to the active compounds, may also contain suspending agents, for example ethoxylated isostearyl alcohol, polyoxyethylene sorbitol and polyoxyethylene sorbitan esters, microcrystalline cellulose, partial aluminum hydroxide, bentonite, agar and gum tragacanth, or mixtures of these substances, etc.

In some cases, to extend the effect of drugs, slowing the absorption of subcutaneous or intramuscular injectable drugs is expected. This can be achieved by use of liquid suspensions of a poorly water-soluble crystalline or amorphous substance. As such, drug absorption rate depends on the dissolution rate, while the dissolution rate may also depend on crystal size and crystalline form. Alternatively, delayed absorption of the drug form in parenteral administration is achieved by dissolving or suspending the drug in an oil vehicle.

Injectable depot formulation forms may be prepared by forming microcapsule matrix of drug in biodegradable polymers such as polylactide-polyglycolide. According to the ratio of the drug to the polymers and properties of the specific polymers employed, drug release rate can be controlled. Other examples of biodegradable polymers include poly (orthoesters) and poly(anhydrides). Injectable depot formulations also can be prepared by embedding the drug into liposomes or microemulsions compatible with body tissues.

Injectable formulations may be sterilized for example by filtration with a bacteria filter or by incorporating a sterilizing agent in the form of sterile solid composition. The solid composition may be dissolved or dispersed in sterile water or other sterile injectable medium just prior to administration.

The compound of the present invention or the composition thereof may employ oral method or parenteral administration mode. Oral administration may be tablets, capsules, coating agents, and parenteral administration formulations include injections and suppositories, etc. These formulations are prepared in accordance with methods well known by those skilled in the art. In order to manufacture tablets, capsules, coating agents excipients being used are conventional excipients, for example starch, gelatin, gum acacia, silica, polyethylene glycol, solvents used in liquid dosage forms such as water, ethanol, propylene glycol, vegetable oils (such as maize oil, peanut oil and olive oil, etc.). In the formulations containing the compounds of the present invention, there are also other adjuvants, such as surfactants, lubricants, disintegrants, preservatives, corrigents and pigments, etc. The dosage of the compound of formula I of the present invention contained in tablets, capsules, coating agents, injections and suppositories is calculated based on amount of the compound present in a unit dosage form. In the unit dosage form the general amount of the compound of formula I of the present invention is 0.01-5000 mg, a preferred unit dosage form contains 0.1-500 mg, and a more preferred unit dosage form contains 1-300 mg. Specifically, the solid dosage forms for oral administration provided by the present invention include capsules, tablets, pills, powders and granules. In such solid dosage forms, the active compound may be mixed with at least one inert and pharmaceutically acceptable excipient or carrier such as sodium citrate or dicalcium phosphate and/or the following substances: a) fillers or extenders such as starch, lactose, sucrose, glucose, mannitol and silicic acid; b) binders such as carboxymethylcellulose, alginates, gelatin, polyvinylpyrrolidone, sucrose and gum acacia; c) moisturizers such as glycerol; d) disintegrating agent such as agar, calcium carbonate, potato or tapioca starch, alginic acid, some silicates, and sodium carbonate; e) solution blockers such as paraffin; f) absorption accelerators such as quaternary ammonium compounds; g) wetting agents such as cetyl alcohol and glycerol monostearate; h) adsorbents such as kaolin and bentonite and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

A solid composition of similar type uses excipients for example lactose and polyethylene glycol with high molecular weight, which may be used as an infilling in soft capsules and hard capsules.

The solid dosage forms of tablets, dragees, capsules, pills and granules may be prepared together with coatings and casing materials such as enteric coating materials and other coating materials commonly known in the field of medical formulations.

These solid dosage forms may optionally contain opacifying agents, and the constitutions thereof can also make them release active ingredients merely or preferably in a certain site of intestinal tract optically in delayed mode. Examples of embedding composition that can be used include substances with high molecular weight and waxes. If appropriate, the active compounds can be formulated into microcapsule forms with one or more excipients above.

Liquid dosage forms for oral administration include pharmaceutically acceptable emulsions, solutions, suspensions, syrups and elixirs. Liquid dosage forms, in addition to the active compounds, also contain inert diluents commonly used in the art e.g. water or other solvents, solubilizers and emulsifiers for example ethanol, isopropanol, ethyl carbonate, ethyl acetate, benzyl alcohol, benzyl benzoate, propylene glycol, 1,3-butanediol, dimethylformamide, oils (particularly cottonseed oil, peanut oil, maize oil, germ oil, olive oil, castor oil and sesame oil), glycerol, tetrahydrofurfuryl alcohol, polyethylene glycols and sorbitan fatty acid esters and mixtures thereof. In addition to inert diluents oral compositions may also contain excipients, such as wetting agents, emulsifiers and suspending agents, sweetening agents, corrigents and flavoring agents.

Compositions for rectal or vaginal administration are preferably suppositories. Suppositories may be prepared by mixing the compounds of the present invention with suitable non-irritating excipients or carriers such as cocoa butter, polyethylene glycols or suppository waxes. They are solid at room temperature but liquid at body temperature therefore able to melt in rectal cavity or vaginal cavity then releasing the active compounds.

The compounds of the present invention and the compositions thereof are also considered for topical administration. The dosage forms for topically administrating the compounds of the present invention include powders, sprays, ointments and inhalants. Under a sterile condition the active compounds are mixed with pharmaceutically acceptable carriers and any required preservatives, buffers or propellants. Ophthalmic formulations, ophthalmic ointments, powders and solutions are also considered within the scope of the present invention.

The compounds of the present invention may also be administered in the form of liposomes. As commonly known in the art, liposomes are usually prepared with phospholipids or other lipid substances. Liposomes are formed of single-layer or multi-layer hydration liquid crystals dispersed in an aqueous medium. Any non-toxic physiologically acceptable and metabolizable lipid able to form liposomes may be used. The compositions of the present invention in liposomes form, in addition to the compounds of the present invention, may also contain stabilizers, preservatives, excipients, etc. The preferred lipids are natural and synthetic phospholipids and phosphatidylcholine (lecithin), which may be used separately or together. Methods of forming liposomes are commonly known in the art. See for example Prescott, Ed., Methods in Cell Biology, Volume XIV, Academic Press, New York, N.Y. (1976), p. 33.

The structures and the activities of glycine reuptake inhibitory effect of some exemplary compounds of the present invention are listed below, wherein the method for determining anti-glycine reuptake activity is shown in the assays below. These results indicate that the compounds of the present invention are effective glycine reuptake inhibitors and can be used to treat schizophrenic disorder.

EMBODIMENTS

Hereinafter the present invention is further illustrated through the specific preparation embodiments and biological tests. However, it should be understood that these examples and test examples are merely for the use of more detailed and specific illustration, and should not be construed to be used in any form of limiting the present invention.

The present invention conducts a general and/or specific description on the materials used in the tests and test methods. Although many materials and operation methods used to achieve the purposes of the present invention are commonly known in the art, the present invention still makes a description detailedly as possible here. It should be clear to those skilled in the art, hereinafter if without particular description, the materials and operation methods used in the present invention are commonly known in the art.

EXAMPLE 1

Preparation of Compounds of the Following Formula (Co. 1)

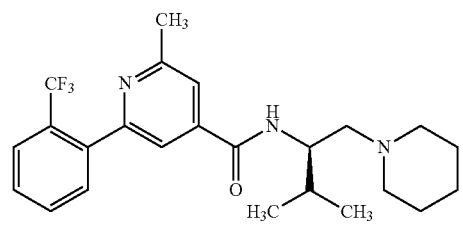

The synthetic route is as follows:

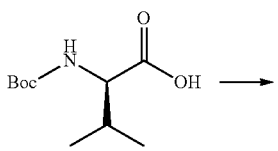

-continued

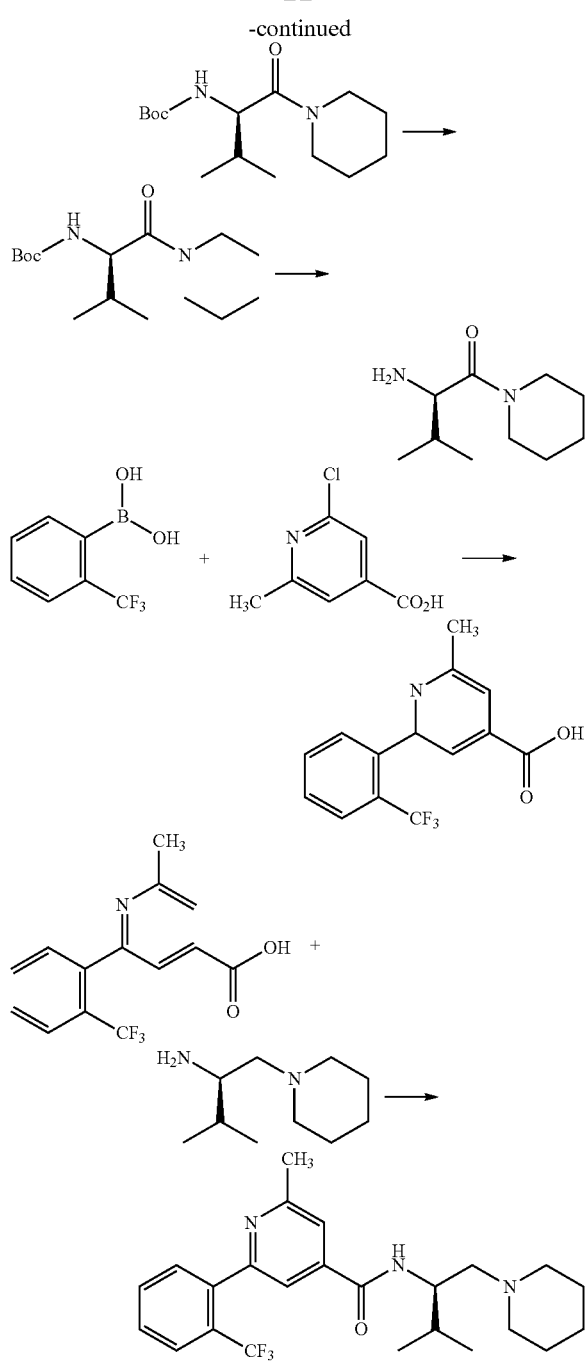

Specific steps:

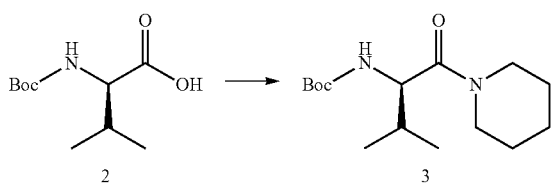 [SMILES: CC(C)[C@@H](NC(=O)OC(C)(C)C)C(=O)O ; CC(C)[C@@H](NC(=O)OC(C)(C)C)C(=O)N1CCCCC1]

Operations: 10 g of compound 2 (N-Boc-L-valine, from Yuchen Chemical Technology Research Institute, Laiyang) was dissolved in dichloromethane. 1-ethyl-(3-dimethylaminopropyl) carbodiimide (Chongqing Werlchem Fine Chemical Co., Ltd.) and N,N-diisopropylethylamine (Shanghai Linger Chemical Co., Ltd) were added and reacted for 30 min. 1.2 eq of piperidine was added and the reaction was completed. The system was filtrated and the solvent was evaporated. The residue was dissolved in 20 mL of ethyl acetate, washed with dilute HCl, then washed with a saturated aqueous solution of NaHCO₃, and then washed with brine. The resulting substance was dried, filtered and desolventized to obtain a pale-yellow oily substance (compound 3).

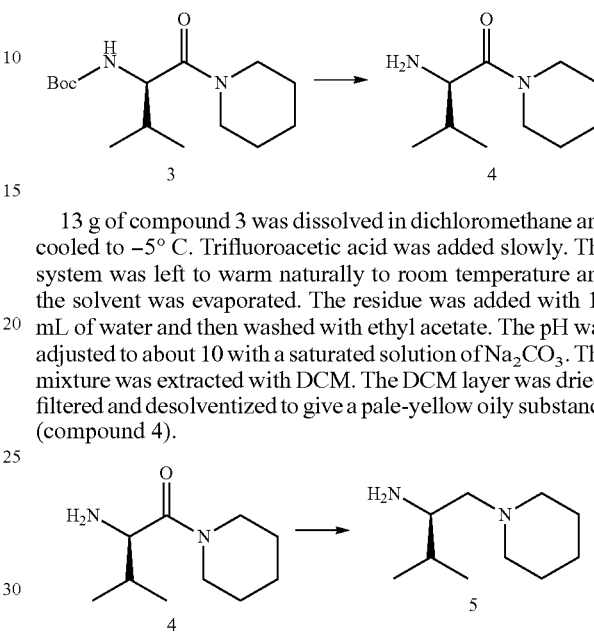

13 g of compound 3 was dissolved in dichloromethane and cooled to −5° C. Trifluoroacetic acid was added slowly. The system was left to warm naturally to room temperature and the solvent was evaporated. The residue was added with 10 mL of water and then washed with ethyl acetate. The pH was adjusted to about 10 with a saturated solution of Na₂CO₃. The mixture was extracted with DCM. The DCM layer was dried, filtered and desolventized to give a pale-yellow oily substance (compound 4).

30 ml of THF was added to LiAlH₄, generating a large number of bubbles, and cooled to −10° C. 5.6 g of compound 4 was added dropwise slowly and the temperature was maintained below 0° C. After the reaction was completed, the reaction system was quenched by sequentially adding water at 0° C., and filtered. The resulting filter cake was washed with THF, the mother liquor was evaporated off solvent. The residue was dissolved in ethyl acetate, dried with anhydrous magnesium sulfate, filtered and desolventized to obtain an oily product (compound 5).

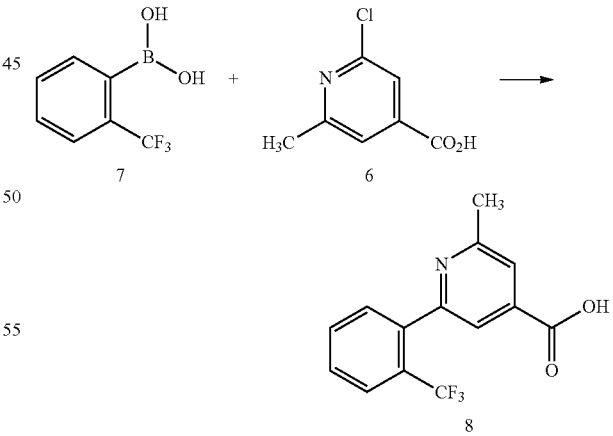

1.0 g of compound 6 (2-chloro-6-methyl-4-picolinic acid, from Hangzhou Banghua Imp. &Exp. Co. Ltd.), 2.21 g of compound 7 (2-(trifluoromethyl)phenylboronic acid, from Shanghai Yiji Industries Co., Ltd.), K₂CO₃ and Pd(PPh₃)Cl₂ were added to a reaction flask with N₂ protection, followed by sequentially adding H₂O, DMF, and heated to 90° C., tracked by TLC. After the reaction was completed, the system was filtered. The resulting filter cake was washed with water. The filtrate was added with water and the aqueous phase was washed with ethyl acetate and adjusted to be acidic with hydrochloric acid to precipitate a yellow solid. The yellow solid was obtained by filtration and recrystallized with ethanol to obtain a light yellow solid (compound 8).

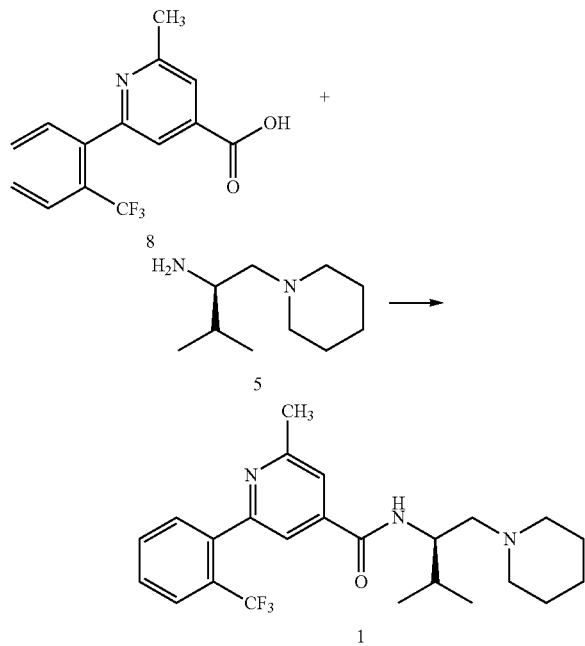

2.2 g of compound 8 was dissolved in 30 mL THF and SOCl$_2$, 2 drops of catalytic DMF were added, heated and refluxed for 1 hour, and cooled to 5° C. Compound 5 and triethylamine were added, heated to room temperature and reacted for 30 min, tracked and monitored by TLC until the reaction was completed. The system was filtered and the solvent was evaporated. The residue was dissolved in 30 mL of ethyl acetate, washed with a saturated aqueous solution of Na$_2$CO$_3$ and then washed with water. Ethyl acetate was separated and concentrated to precipitate a solid. A white solid was obtained by filtration and dried to obtain the target compound 1 (i.e. Co. 1).

Nuclear magnetic resonance H spectrum of the compound (Co. 1):

1H-NMR (CDCl$_3$): δ7.783~7.260 (m, 6H, Ar—H), δ4.086 (s, 1H, NH), δ 2.268 (s, 3H, Ar—CH$_3$), δ 2.489-2.343 (t, 6H, N—(CH$_2$)$_3$), δ 2.165-2.117 (d, 1H, N—CH), Δ1.522-1.421 (d, 6H, (CH$_2$)$_3$), δ0.965-0.948 (d, 6H, (CH$_3$)$_2$),

EXAMPLE 2

Preparation of Compounds of the Following Formula (Co. 2)

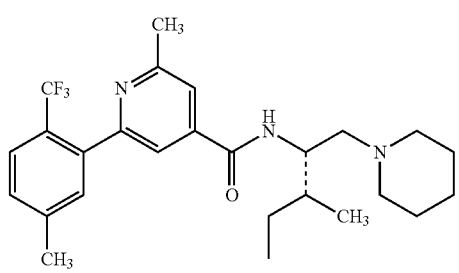

The synthetic route is as follows:

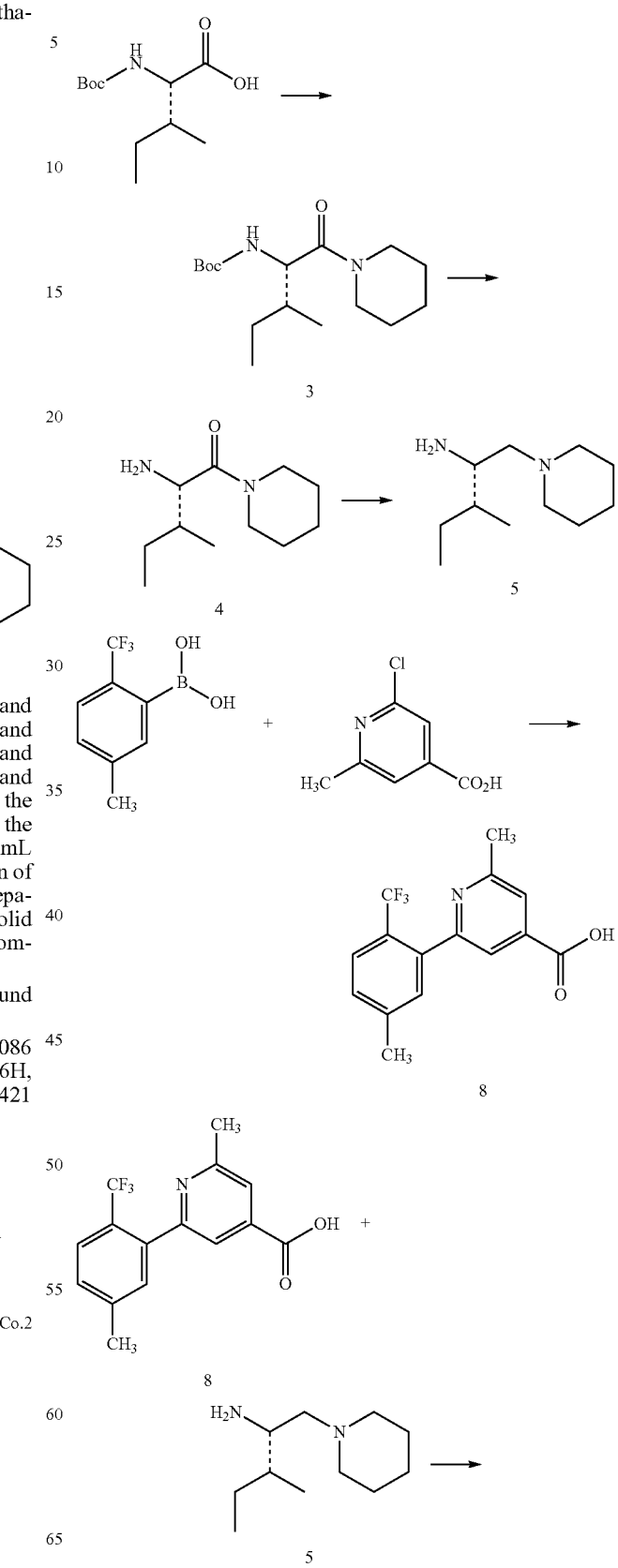

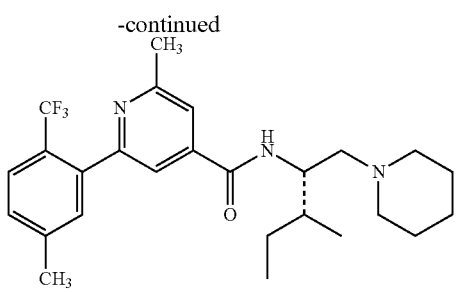

Operations: 10 g of N-Boc-D-isoleucine (Chengdu Aikeda Chemical Reagent Co., Ltd.) was dissolved in dichloromethane. Methyl clhloroformate (Hunan Dejia Biochemical Technology Co., Ltd.) and N-methyl morpholine (Nanjing Oriental Chemical Co., Ltd.) were added and reacted for 60 min. 1.2 ep of piperidine was added and the reaction was completed. The system was filtrated and the solvent was evaporated. The residue was dissolved in 20 mL of ethyl acetate, washed with dilute HCl, then washed with a saturated aqueous solution of $NaHCO_3$, and then washed with brine. The resulting substance was dried, filtered and desolventized to obtain a pale-yellow oily substance (compound 3).

13 g of compound 3 was dissolved in dichloromethane and cooled to −5° C. Trifluoroacetic acid was added slowly. The system was left to warm naturally to room temperature and the solvent was evaporated. The residue was combined with the aqueous phase, added 10 mL of water and then washed with ethyl acetate. pH was adjusted to about 10 with a saturated solution of $Na_2CO_3$. The mixture was extracted with DCM. The DCM layer was dried, filtered and desolventized to give a pale-yellow oily substance (compound 4).

30 ml of THF was added to $LiAlH_4$, generating a large number of bubbles, and cooled to −10° C. 5.6 g of compound 4 was added dropwise slowly and the temperature was maintained below 0° C. After the reaction was completed, the reaction system was quenched by sequently adding water at 0° C., and filtered. The resulting filter cake was washed with THF, the mother liquor was evaporated off solvent. The residue was dissolved in ethyl acetate, dried with anhydrous magnesium sulfate, filtered and desolventized to obtain an oily product (compound 5).

1.0 g of 2-chloro-6-methyl-4-picolinic acid (Hangzhou Banghua Imp. &Exp. Co. Ltd.), 2.5 g of 2-(trifluoromethyl)-4-methyl-phenylboronic acid as well as $K_2CO_3$ and $Pd(PPh_3)Cl_2$ were added to a reaction flask with $N_2$ protection, followed by sequentially adding $H_2O$, DMF, and heated to 90° C., tracked by TLC. After the reaction was completed, the system was filtered. The resulting filter cake was washed with water. The filtrate was added with water and the aqueous phase was washed with ethyl acetate and adjusted to be acidic with hydrochloric acid to precipitate a yellow solid. The yellow solid was obtained by filtration and recrystallized with ethanol to obtain a light yellow solid (compound 8).

2.2 g of compound 8 was dissolved in 30 mL THF and $SOCl_2$, 2 drops of catalytic DMF were added, heated and refluxed for 1 hour, and cooled to 5° C. Compound 5 and triethylamine were added, heated to room temperature and reacted for 30 min, tracked and monitored by TLC until the reaction was completed. The system was filtered and the solvent was evaporated. The residue was dissolved in 30 mL of ethyl acetate, washed with a saturated aqueous solution of $Na_2CO_3$ and then washed with water. Ethyl acetate was separated and concentrated to precipitate a solid. A white solid was obtained by filtration and dried to obtain the target compound Co. 2.

Nuclear magnetic resonance H spectrum of the compound (Co. 2):

1H-NMR ($CDCl_3$): δ8.0 (s, 1H), δ7.01~7.96 (m, 6H), δ3.81 (d, 1H), δ 2.35 (s, 3H), δ 2.24-2.58 (t, 6H), δ1.522-1.421 (d, 6H), δ 0.965-0.948 (d, 6H), δ1.29 (s, 2H), δ0.96-1.06 (m, 6H)

EXAMPLE 3

Preparation of Compounds of Following Formula (Co. 3)

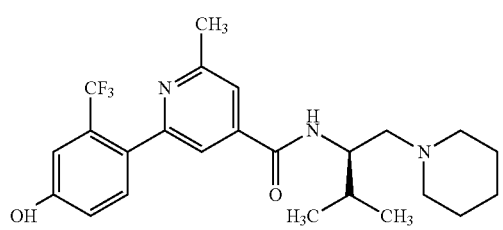

The synthetic route is as follows:

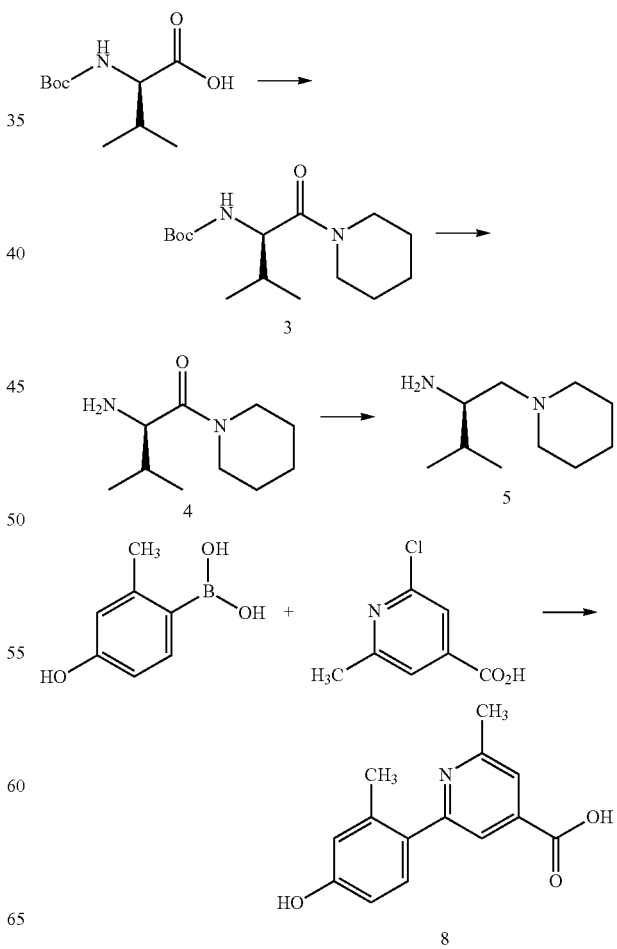

-continued

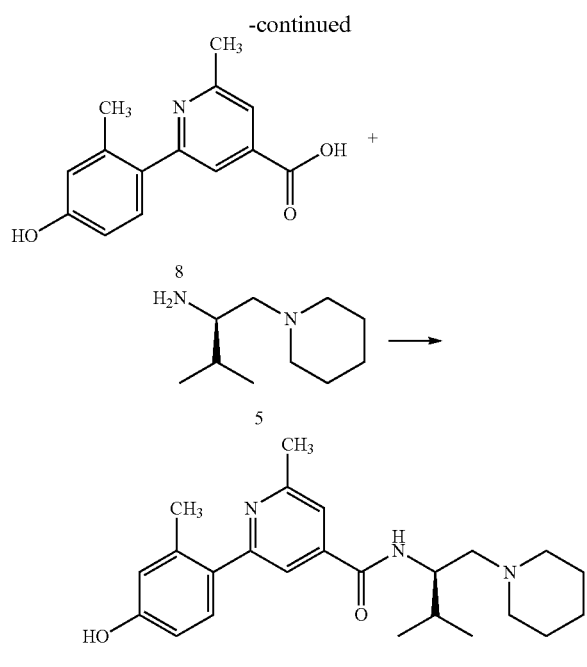

Operations: 10 g of compound 2 (N-Boc-L-valine, from Yuchen Chemical Technology Research Institute, Laiyang) was dissolved in dichloromethane. 1-ethyl-(3-dimethylaminopropyl) carbodiimide (Chongqing Werlchem Fine Chemical Co., Ltd.) and N,N-diisopropylethylamine (Shanghai Linger Chemical Co., Ltd) were added and reacted for 30 min. 1.2 ep of piperidine was added and the reaction was completed. The system was filtrated and the solvent was evaporated. The residue was dissolved in 20 mL of ethyl acetate, washed with dilute HCl, then washed with a saturated aqueous solution of $NaHCO_3$, and then washed with brine. The resulting substance was dried, filtered and desolventized to obtain a pale-yellow oily substance (compound 3).

13 g of compound 3 was dissolved in dichloromethane and cooled to −5° C. Trifluoroacetic acid was added slowly. The system was left to warm naturally to room temperature and the solvent was evaporated. The residue was combined with the aqueous phase, added 10 mL of water and then washed with ethyl acetate. pH was adjusted to about 10 with a saturated solution of $Na_2CO_3$. The mixture was extracted with DCM. The DCM layer was dried, filtered and desolventized to give a pale-yellow oily substance (compound 4).

30 ml of THF was added to $LiAlH_4$, generating a large number of bubbles, and cooled to −10° C. 5.6 g of compound 4 was added dropwise slowly and the temperature was maintained below 0° C. After the reaction was completed, the reaction system was quenched by sequently adding water at 0° C., and filtered. The resulting filter cake was washed with THF, the mother liquor was evaporated off solvent. The residue was dissolved in ethyl acetate, dried with anhydrous magnesium sulfate, filtered and desolventized to obtain an oily product (compound 5).

1.0 g of compound 6 (2-chloro-6-methyl-4-picolinic acid, from Hangzhou Banghua Imp. &Exp. Co. Ltd.), 2.4 g of 4-hydroxyl-2-methyl-phenylboronic acid as well as $K_2CO_3$ and $Pd(PPh_3)Cl_2$ were added to a reaction flask with $N_2$ protection, followed by sequentially adding $H_2O$, DMF, and heated to 90° C., tracked by TLC. After the reaction was completed, the system was filtered. The filter cake was washed with water. The filtrate was added with water and the aqueous phase was washed with ethyl acetate and adjusted to be acidic with hydrochloric acid to precipitate a yellow solid. The yellow solid was obtained by filtration and recrystallized with ethanol to obtain a light yellow solid (compound 8).

2.2 g of compound 8 was dissolved in 30 mL THF and $SOCl_2$, 2 drops of catalytic DMF were added, heated and refluxed for 1 hour, and cooled to 5° C. Compound 5 and triethylamine were added, heated to room temperature and reacted for 30 min, tracked and monitored by TLC until the reaction was completed. The system was filtered and the solvent was evaporated. The residue was dissolved in 30 mL of ethyl acetate, washed with a saturated aqueous solution of $Na_2CO_3$ and then washed with water. Ethyl acetate was separated and concentrated to precipitate a solid. A white solid was obtained by filtration and dried to obtain the target compound Co. 3.

Nuclear magnetic resonance H spectrum of the compound (Co. 3):

1H-NMR ($CDCl_3$): δ7.98.0 (s, 1H), δ6.62~7.96 (m, 6H), δ5.0 (d, 1H), δ 3.81 (d, 1H), δ 2.35-2.55 (m, 6H), δ 2.24-2.58 (t, 6H), δ 1.432-1.571 (d, 6H), δ0.96-1.01 (m, 6H)

EXAMPLE 4

Preparation of Compounds of Following Formula (Co. 4)

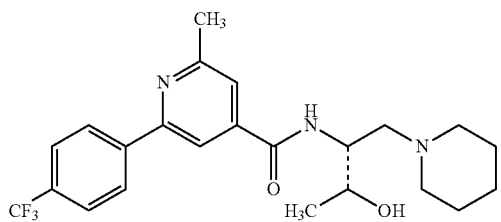 [SMILES: Cc1cc(C(=O)N[C@H](CN2CCCCC2)C(C)O)cc(-c2ccc(C(F)(F)F)cc2)n1]

The synthetic route is as follows:

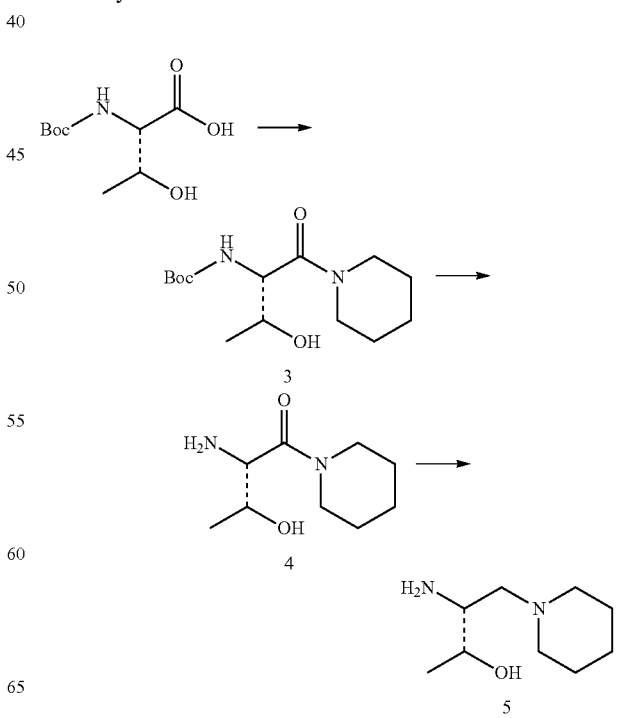

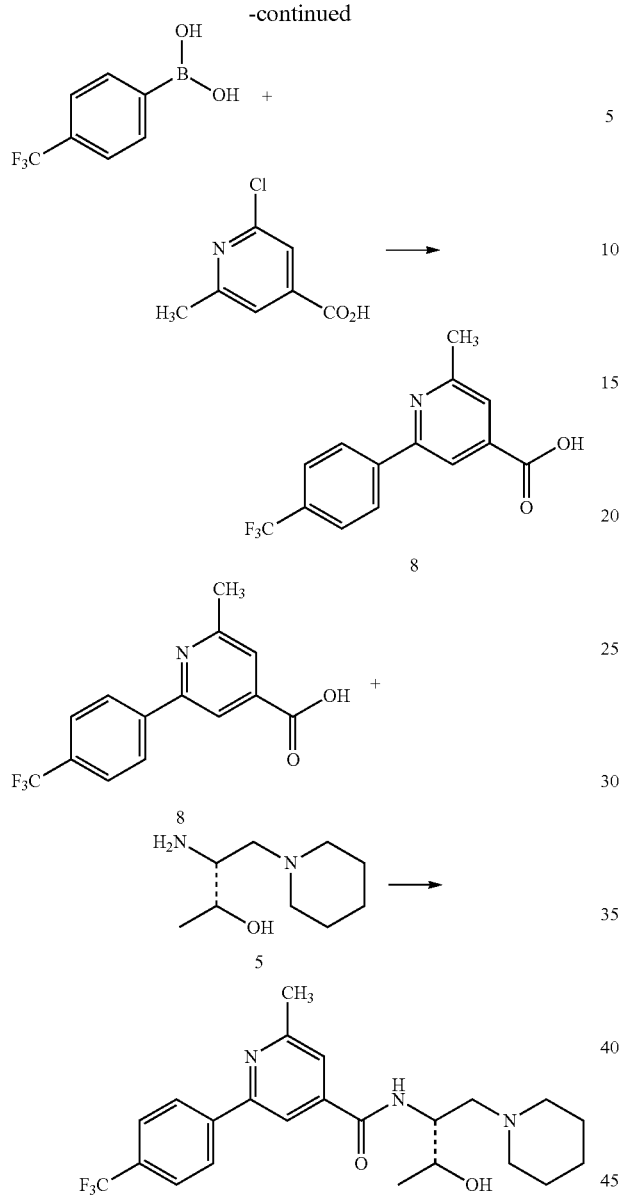

Operations: 10 g of N-Boc-D-threonine (Nantong Qihai Chemical Co. Ltd.) was dissolved in dichloromethane. Methyl clhloroformate (Hunan Dejia Biochemical Technology Co., Ltd.) and N-methyl morpholine (Nanjing Oriental Chemical Co., Ltd.) were added and reacted for 60 min. 1.2 ep of piperidine was added and the reaction was completed. The system was filtrated and the solvent was evaporated. The residue was dissolved in 20 mL of ethyl acetate, washed with dilute HCl, then washed with a saturated aqueous solution of NaHCO$_3$, and then washed with brine. The resulting substance was dried, filtered and desolventized to obtain a pale-yellow oily substance (compound 3).

13 g of compound 3 was dissolved in dichloromethane and cooled to −5° C. Trifluoroacetic acid was added slowly. The system was left to warm naturally to room temperature and the solvent was evaporated. The residue was combined with the aqueous phase, added 10 mL of water and then washed with ethyl acetate. pH was adjusted to about 10 with a saturated solution of Na$_2$CO$_3$. The mixture was extracted with DCM. The DCM layer was dried, filtered and desolventized to give a pale-yellow oily substance (compound 4).

30 ml of THF was added to LiAlH$_4$, generating a large number of bubbles, and cooled to −10° C. 5.6 g of compound 4 was added dropwise slowly and the temperature was maintained below 0° C. After the reaction was completed, the reaction system was quenched by sequently adding water at 0° C., and filtered. The resulting filter cake was washed with THF, the mother liquor was evaporated off solvent. The residue was dissolved in ethyl acetate, dried with anhydrous magnesium sulfate, filtered and desolventized to obtain an oily product (compound 5).

1.0 g of 2-chloro-6-methyl-4-picolinic acid (Hangzhou Banghua Imp. &Exp. Co. Ltd.), 2.1 g of 2-trifluoromethyl phenylboronic acid as well as K$_2$CO$_3$ and Pd(PPh$_3$)Cl$_2$ were added to a reaction flask with N$_2$ protection, followed by sequentially adding H$_2$O, DMF, and heated to 90° C., tracked by TLC. After the reaction was completed, the system was filtered. The resulting filter cake was washed with water. The filtrate was added with water and the aqueous phase was washed with ethyl acetate and adjusted to be acidic with hydrochloric acid to precipitate a yellow solid. The yellow solid was obtained by filtration and recrystallized with ethanol to obtain a light yellow solid (compound 8).

2.2 g of compound 8 was dissolved in 30 mL THF and SOCl$_2$, 2 drops of catalytic DMF were added, heated and refluxed for 1 hour, and cooled to 5° C. Compound 5 and triethylamine were added, heated to room temperature and reacted for 30 min, tracked and monitored by TLC until the reaction was completed. The system was filtered and the solvent was evaporated. The residue was dissolved in 30 mL of ethyl acetate, washed with a saturated aqueous solution of Na$_2$CO$_3$ and then washed with water. Ethyl acetate was separated and concentrated to precipitate a solid. A white solid was obtained by filtration and dried to obtain the target compound Co. 4.

Nuclear magnetic resonance H spectrum of the compound (Co. 4):

1H-NMR (CDCl$_3$), δ7.94.0 (s, 1H), δ7.12~7.99 (m, 6H), δ3.90 (d, 1H), δ 2.34-2.65 (m, 6H), δ 2.24 (s, 1H), δ 2.15-2.21 (t, 6H), δ 1.432-1.571 (d, 6H), δ1.21-1.23 (d, 3H)

EXAMPLE 5

Preparation of Compounds of Following Formula (Co. 5)

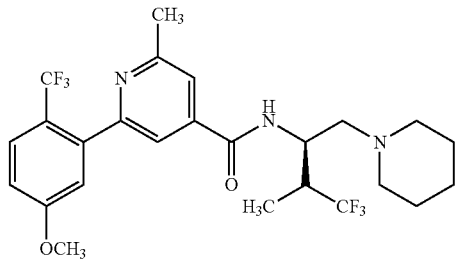 [SMILES: COc1ccc(C(F)(F)F)c(-c2cc(C(=O)N[C@@H](CN3CCCCC3)C(C)C(F)(F)F)cc(C)n2)c1]

The synthetic route is as follows:

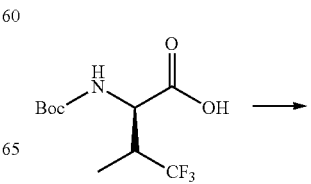

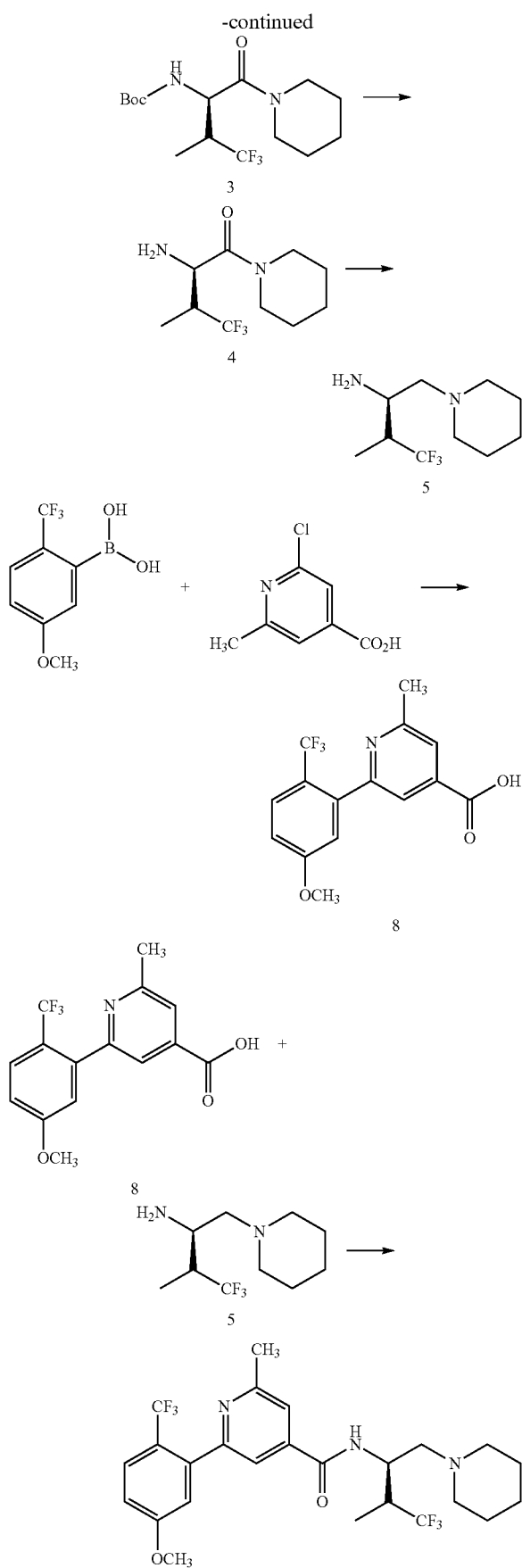

Operations: 10 g of compound 2 (L-N-Boc-2-amino-3-trifluoromethyl n-butyric acid, from Yuchen Chemical Technology Research Institute, Laiyang) was dissolved in dichloromethane. 1-ethyl-(3-dimethylaminopropyl) carbodiimide (Chongqing Werlchem Fine Chemical Co., Ltd.) and N,N-diisopropylethylamine (Shanghai Linger Chemical Co., Ltd) were added and reacted for 30 min. 1.2 ep of piperidine was added and the reaction was completed. The system was filtrated and the solvent was evaporated. The residue was dissolved in 20 mL of ethyl acetate, washed with dilute HCl, then washed with a saturated aqueous solution of $NaHCO_3$, and then washed with brine. The resulting substance was dried, filtered and desolventized to obtain a pale-yellow oily substance (compound 3).

13 g of compound 3 was dissolved in dichloromethane and cooled to −5° C. Trifluoroacetic acid was added slowly. The system was left to warm naturally to room temperature and the solvent was evaporated. The residue was combined with the aqueous phase, added 10 mL of water and then washed with ethyl acetate. pH was adjusted to about 10 with a saturated solution of $Na_2CO_3$. The mixture was extracted with DCM. The DCM layer was dried, filtered and desolventized to give a pale-yellow oily substance (compound 4).

30 ml of THF was added to $LiAlH_4$, generating a large number of bubbles, and cooled to −10° C. 5.6 g of compound 4 was added dropwise slowly and the temperature was maintained below 0° C. After the reaction was completed, the reaction system was quenched by sequently adding water at 0° C., and filtered. The resulting filter cake was washed with THF, the mother liquor was evaporated off solvent. The residue was dissolved in ethyl acetate, dried with anhydrous magnesium sulfate, filtered and desolventized to obtain an oily product (compound 5).

1.0 g of compound 6 (2-chloro-6-methyl-4-picolinic acid, from Hangzhou Banghua Imp. &Exp. Co. Ltd.), 2.4 g of 5-methoxy-2-trifluoromethyl-phenylboronic acid as well as $K_2CO_3$ and $Pd(PPh_3)Cl_2$ were added to a reaction flask with $N_2$ protection, followed by sequentially adding $H_2O$, DMF, and heated to 90° C., tracked by TLC. After the reaction was completed, the system was filtered. The resulting filter cake was washed with water. The filtrate was added with water and the aqueous phase was washed with ethyl acetate and adjusted to be acidic with hydrochloric acid to precipitate a yellow solid. The yellow solid was obtained by filtration and recrystallized with ethanol to obtain a light yellow solid (compound 8).

2.2 g of compound 8 was dissolved in 30 mL THF and $SOCl_2$, 2 drops of catalytic DMF were added, heated and refluxed for 1 hour, and cooled to 5° C. Compound 5 and triethylamine were added, heated to room temperature and reacted for 30 min, tracked and monitored by TLC until the reaction was completed. The system was filtered and the solvent was evaporated. The residue was dissolved in 30 mL of ethyl acetate, washed with a saturated aqueous solution of $Na_2CO_3$ and then washed with water. Ethyl acetate was separated and concentrated to precipitate a solid. A white solid was obtained by filtration and dried to obtain the target compound Co. 5.

Nuclear magnetic resonance H spectrum of the compound (Co. 5):

1H-NMR ($CDCl_3$): δ8.14 (s, 1H), δ6.65~7.99 (m, 4H), δ3.84 (d, 1H), δ3.73 (s, 3H), δ2.56 (s, 3H), δ2.23-2.59 (t, 6H), δ1.31-1.41 (d, 6H), δ1.01-1.09 (m, 6H).

The pharmaceutical effect of the synthesized compounds was fully evaluated by biological tests. The results indicated that the test compound had a significant inhibitory effect on high spontaneous activity in rats induced by PCP or Amphetamine, and the active level thereof was better than a positive drug, which indicated that the test compound might possess a stronger effect of anti-schizophrenic positive symptoms. The test compound had no significant effect on spontaneous activity in rats, indicating that the test compound might not have undue sedation.

TEST EXAMPLE 1

Effect of Test Compound on Spontaneous Activity in Rats (LMA)

Animals used for experiments were adult male Wistar rats weighing 180~250 g, housed in groups of 6/cages, regulated with a 12/12 hour light/dark cycle, maintained at a constant temperature of 23±1° C. and a humidity of 50~60% and allowed ad libitum access to rodent chow and water. After animals were purchased from the Experimental Animal Center, an adaptive housing was performed for a week, all the animals were randomly divided into two groups:

Group one: negative control group, intraperitoneally injected with 1% DMSO in physiological saline (10.0 ml/kg, i.p.);

Group two: experimental drug group, the rats were intraperitoneally injected respectively with different doses of test compound Co. 1: 5.0, 10 and 30 mg/kg, i.p., the drug was formulated in 1% DMSO in physiological saline.

The experiment employed Shanghai Jiliang animal behavior video analysis system, wherein the experimental environment was kept absolutely silent, when grabbing animals and administrating, movements were gentle to minimize adverse reactions of mental condition and emotion brought by external stimulus. 60 minutes after administration, the rats were placed in a spontaneous activity box, which was placed in an absolutely silent environment. The spontaneous activity box was connected to a recording apparatus and the activity conditions of rats were recorded for 30-60 minutes. The effect of drug or control on spontaneous activity in rats was determined.

TABLE 1

The effect of the test compound Co. 1 on spontaneous activity in normal rats

| Treatment | total distance within one hour (meter) |
|---|---|
| Vehicle | 25.3 ± 3.2 |
| Olanzepine 10 mg/kg. i.p. | 24.6 ± 5.8 |
| Test compound Co. 1 5 mg/kg. i.p. | 24.9 ± 6.2 |
| Test compound Co. 1 10 mg/kg. i.p. | 22.4 ± 4.0 |
| Test compound Co. 1 20 mg/kg. i.p. | 23.8 ± 5.2 |

The experimental results were expressed by means ± s.e. means, Dunnett's test.

Results: test compound Co. 1 had no significant effect on spontaneous activity in normal rats (P>0.05, Dunnett's test), which indicated that the compound had no undue sedation.

Olanzepine also had no effect on spontaneous activity in normal rats.

TEST EXAMPLE 2

Effect of Test Compound on High-Activity Behaviors in Rats Induced by PCP

Animals used for experiments were adult male Wistar rats weighing 180~250 g, housed in group of 6/cages, regulated with a 12/12 hour light/dark cycle, maintained at a constant temperature of 23±1° C. and a humidity of 50~60% and allowed ad libitum access to rodent chow and water. After animals were purchased from the Experimental Animal Center, an adaptive housing was performed for a week, all the animals were randomly divided into three groups:

Group 1: negative control group, intraperitoneally injected with 1% DMSO in physiological saline (2 ml/kg, i.p.);

Group 2: experimental drug group, the rats were intraperitoneally injected respectively with different doses of test compound Co. 1: 5.0, 10 and 30 mg/kg, i.p., the drug was formulated in 1% DMSO in physiological saline.

Group 3: positive drug control group, the rats were intraperitoneally injected with Olanzepine (10 mg/kg, i.p., the drug was formulated in 1% DMSO in physiological saline)

The experiment employed Shanghai Jiliang animal behavior video analysis system, wherein the experimental environment was kept absolutely silent, when grabbing animals and administrating, movements were gentle to minimize adverse reactions of mental condition and emotion brought by external stimulus. The rats were moved from the animal room to a quiet lab and adapted for at least two hours. Subcutaneous injection of PCP (5.0 mg/kg, s.c.), or 1% DMSO in physiological saline as control, was administrated. 30 minutes later, the animals were intraperitoneally injected with the test compound, or 1% DMSO in physiological saline as control. The rats were placed in a spontaneous activity box, which was placed in an absolutely silent environment. The spontaneous activity box was connected to a recording apparatus and the activity conditions of rats were recorded for 30-60 minutes. The effect of drug or control on spontaneous activity in rats was determined.

TABLE 2 the effect of test compound Co. 1 on high-activity behaviors in rat induced by PCP

| Treatment | LMA (total distance within one hour (meter)) |
|---|---|
| Vehicle + vehicle | 28.9 ± 6.5 |
| PCP + vehicle | 59.4 ± 8.3** |
| PCP + Olanzepine 10 mg/kg. i.p. | 32.1 ± 5.2## |
| PCP + test compound Co. 1 5 mg/kg. i.p. | 38.6 ± 7.1## |
| PCP + test compound Co. 1 10 mg/kg. i.p. | 26.4 ± 4.0## |
| PCP + test compound Co. 1 30 mg/kg. i.p. | 22.3 ± 3.4## |

The experimental results were expressed by means ± s.e. means, wherein **P < 0.01, PCP group vs. vehicle; ##P < 0.001, drug treating group vs. PCP group, Dunnett's test.

Experimental results: intraperitoneal injection of PCP in rats significantly increased the spontaneous activity in rats (P<0.01, Dunnett's test, compared with the negative control group). Test compound Co. 1 (5, 10 and 30 mg/kg. i.p.) significantly inhibited the high-activity behaviors in rats induced by PCP (P<0.01, Dunnett's test, compared with the PCP treatment group). In the positive drug group, Olanzepine significantly inhibited the high-activity behaviors in rats induced by PCP (P<0.01, Dunnett's test, compared with the PCP group). Compared with the positive drug Olanzepine, the inhibitory effect of the tested compound Co. 1 on high-activity behaviors in rats induced by PCP is stronger (P<0.05, Dunnett's test, compared with the Olanzepine/PCP group).

Conclusions: the experimental results indicated that, the test compound Co. 1 possessed a stronger inhibitory effect on high-activity behaviors in rats induced by PCP, which showed, the compound possessed a better effect of anti-schizophrenic positive symptoms, and this effect was better than Olanzepine.

TEST EXAMPLE 3

Effect of the Test Compound Co. 1 on High-Activity Behaviors in Rats Induced by Amphetamine Animals used for experiments were adult male Wistar rats weighing 180~250 g, housed in group of 6/cages, regulated with a 12/12 hour light/dark cycle, maintained at a constant temperature of 23±1° C. and a humidity of 50~60% and allowed ad libitum access to rodent chow and water. After animals were purchased from the Experimental Animal Center, an adaptive housing was performed for a week, all the animals were randomly divided into three groups:

Group one: negative control group, intraperitoneally injected with 1% DMSO in physiological saline (2 ml/kg, i.p.);

Group two: experimental drug group, the rats were intraperitoneally injected respectively with different amounts of test compound Co. 1: 5, 10 and 30 mg/kg, i.p., the drug was formulated in 1% DMSO in physiological saline.

Group three: positive drug control group, the rats were intraperitoneally injected with Olanzepine (10 mg/kg, i.p., the drug was formulated in 1% DMSO in physiological saline)

The experiment employed Shanghai Jiliang animal behavior video analysis system, wherein the experimental environment was kept absolutely silent, when grabbing animals and administrating, movements were gentle to minimize adverse reactions of mental condition and emotion brought by external stimulus. The rats were moved from the animal room to a quiet lab and adapted for at least two hours. Subcutaneous injection of Amphetamine (1.0 mg/kg, s.c.), or 1% DMSO in physiological saline as control, was administrated. 30 minutes later, the animals were orally administrated of the compound, or physiological saline as control. The rats were placed in a spontaneous activity box, which was placed in an absolutely silent environment. The spontaneous activity box was connected to a recording apparatus and the activity conditions of rats were recorded for 30-60 minutes. The effect of drug or control on spontaneous activity in rats was determined.

TABLE 3

Effect of the test compound Co. 1 on high spontaneous activity in rats induced by Amphetamine

| Treatment | LMA (total distance within one hour (meter)) |
| --- | --- |
| Vehicle + vehicle | 25.6 ± 4.5 |
| AMP + vehicle | 56.2 ± 5.6** |
| AMP + Olanzepine 10 mg/kg. i.p. | 38.4 ± 3.9## |
| AMP + test compound Co. 1 5 mg/kg. i.p. | 39.6 ± 6.0## |
| AMP + test compound Co. 1 10 mg/kg. i.p. | 32.9 ± 6.8## |
| AMP + test compound Co. 1 30 mg/kg. i.p. | 24.6 ± 4.6## |

The experimental results were expressed by means ± s.e. means, wherein **P < 0.01, Aphetamine group vs. vehicle; ##P < 0.001, drug treating group vs. Aphetamine group, Dunnett's test.

Experimental results: intraperitoneal injection of Amphetamine in rats significantly increased the spontaneous activity in rats (P<0.01, Dunnett's test, compared with the negative control group). Test compound Co. 1 (5, 10 and 30 mg/kg. i.p.) significantly inhibited the high-activity behaviors in rats induced by Amphetamine (P<0.01, Dunnett's test, compared with the Amphetamine treatment group). The positive drug Olanzepine significantly inhibited the high-activity behaviors in rats induced by Amphetamine (P<0.01, Dunnett's test, compared with the Amphetamine group). Compared with the positive drug Olanzepine, the inhibitory effect of the test novel compound on high-activity behaviors in rats induced by Amphetamine is stronger (P<0.05, Dunnett's test, compared with the Olanzepine/Amphetamine group).

The invention claimed is:
1. A Compound of formula I:

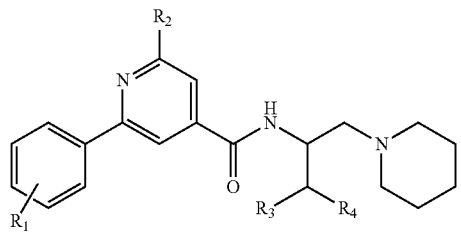

or stereoisomers, pharmaceutically acceptable salts or solvates thereof, wherein R1 is one or more groups selected from the group consisting of hydrogen, halogen, C1-6 alkyl, C1-6 alkoxy, nitro, cyano, amino, hydroxyl, C1-6 haloalkyl, and C1-6 haloalkoxy;

R2 is selected from the group consisting of hydrogen, C1-6 alkyl, C1-6 alkoxy, C1-6 haloalkyl, and C1-6 haloalkoxy;

R3 and R4 are each independently selected from the group consisting of hydrogen, halogen, C1-6 alkyl, C1-6 alkoxy, nitro, cyano, amino, hydroxyl, C1-6 haloalkyl, and C1-6 haloalkoxy.

2. The compound according to claim 1, wherein R1 is one or two groups selected from the group consisting of halogen, hydroxyl, C1-6 alkyl, C1-6 alkoxy, C1-6 haloalkyl and C1-6 haloalkoxy.

3. The compound according to claim 1, wherein R2 is selected from the group consisting of C1-6 alkyl and C1-6 alkoxy.

4. The compound according to claim 1, wherein R3 and R4 are each independently selected from the group consisting of hydrogen, C1-6 alkyl, C1-6 alkoxy and hydroxyl.

5. The compound according to claim 1, wherein the halogen is selected from fluorine, chlorine, bromine and iodine, and the halo is selected from the group consisting of fluorine, chlorine, bromine and iodine.

6. The compound according to claim 5, wherein the halogen is selected from the group consisting of fluorine and chlorine.

7. The compound according to claim 5, wherein the halo is selected from the group consisting of fluorine and chlorine.

8. The compound according to claim 1, wherein the C1-6 alkyl is a C1-4 alkyl.

9. The compound according to claim 1, which is a compound selected from the group consisting of:

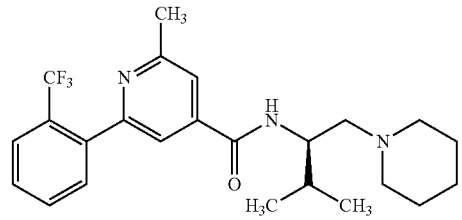

-continued

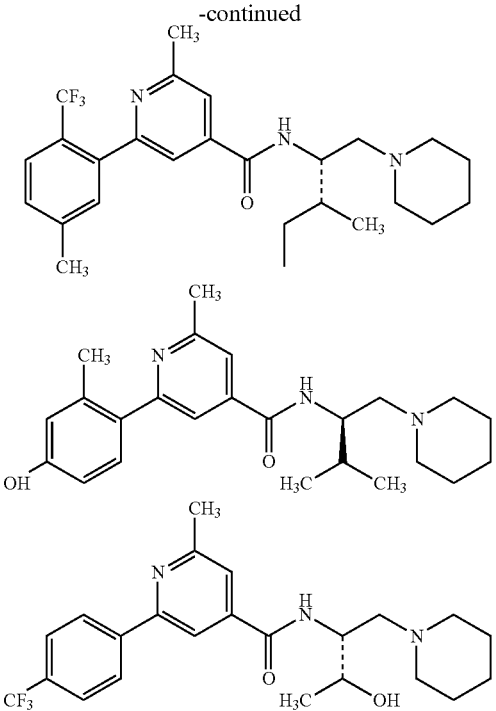

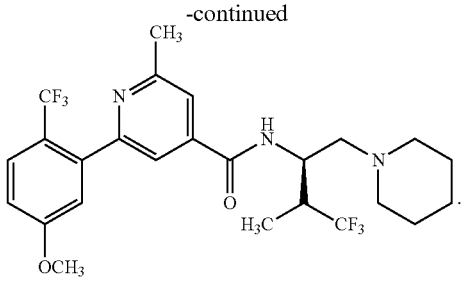

10. A pharmaceutical composition, which comprises the compound of formula I according to claim 1.

11. The pharmaceutical composition according to claim 10, which further comprises one or more pharmaceutically acceptable carriers or excipients.

12. A method for treating schizophrenic disorder in a mammal in need thereof, which comprises administering a therapeutically effective amount of the compound of formula I according to claim 1 to a mammal in need thereof.

13. The method according to claim 12, wherein said mammal is a human.

* * * * *